US00PP23236P3

(12) United States Plant Patent
Kellerhals

(10) Patent No.: US PP23,236 P3
(45) Date of Patent: Dec. 4, 2012

(54) APPLE TREE NAMED 'CH 101'

(50) Latin Name: ***Malus domestica* Borkh**
Varietal Denomination: CH 101

(75) Inventor: Markus Kellerhals, Wädenswil (CH)

(73) Assignee: Agroscope Changins-Wädenswil, Wädenswil (CH)

( * ) Notice: Subject to any disclaimer, the term of this patent is extended or adjusted under 35 U.S.C. 154(b) by 0 days.

(21) Appl. No.: 13/373,536

(22) Filed: Nov. 16, 2011

(65) Prior Publication Data

US 2012/0131706 P1 May 24, 2012

(51) Int. Cl.
*A01H 5/00* (2006.01)

(52) U.S. Cl. ..... Plt./161

(58) Field of Classification Search ..... Plt./161
See application file for complete search history.

*Primary Examiner* — Annette Para
(74) *Attorney, Agent, or Firm* — Michelle Bos

(57) ABSTRACT

A new 'Gala'-type apple variety named 'CH 101.' The new variety is distinguished by its large orange-red fruit, high fruit sugar content, and resistance to scab.

6 Drawing Sheets

Latin name: *Malus domestica* Borkh.
Variety denomination: 'CH 101'.

BACKGROUND OF THE VARIETY

'CH 101' is a new and distinct variety of apple tree. This new variety is a product of a controlled cross made in 1992 at Wädenswil, Switzerland, of 'Gala' (female parent, U.S. Plant Pat. No. 3,637) and 'K1R20A44' (male parent, not patented), and is characterized by its large fruit, high fruit sugar content, and resistance to scab. A seedling resulting from the cross was asexually propagated by grafting in 1994 at Wädenswil, and was subsequently observed over successive asexually propagated generations. The tree and its fruit have been found to remain true to type and to retain the desirable characteristics for which the variety was selected.

BRIEF DESCRIPTION OF THE VARIETY

'CH 101' was first selected for its large fruit, high fruit sugar content, and resistance to scab. It is distinguished from other known Gala-type varieties by these characteristics, as well as by its orange-red over-color.

BRIEF DESCRIPTION OF THE PHOTOGRAPHS

Figure 1:
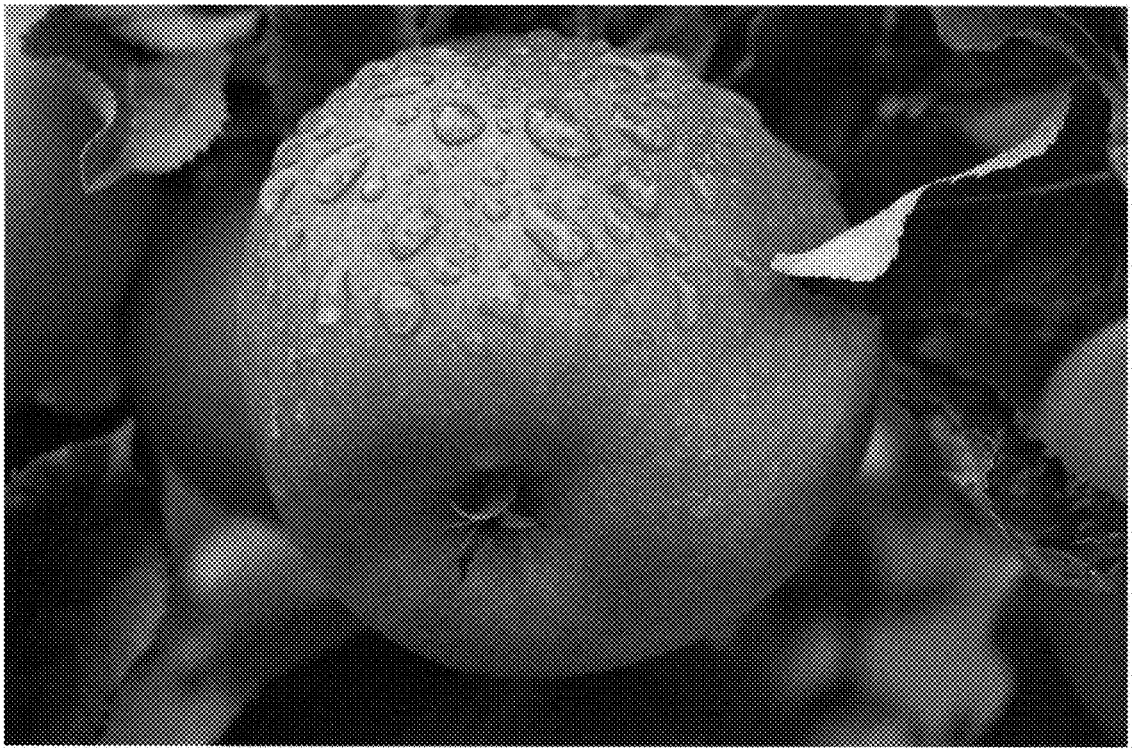
Figure 2:
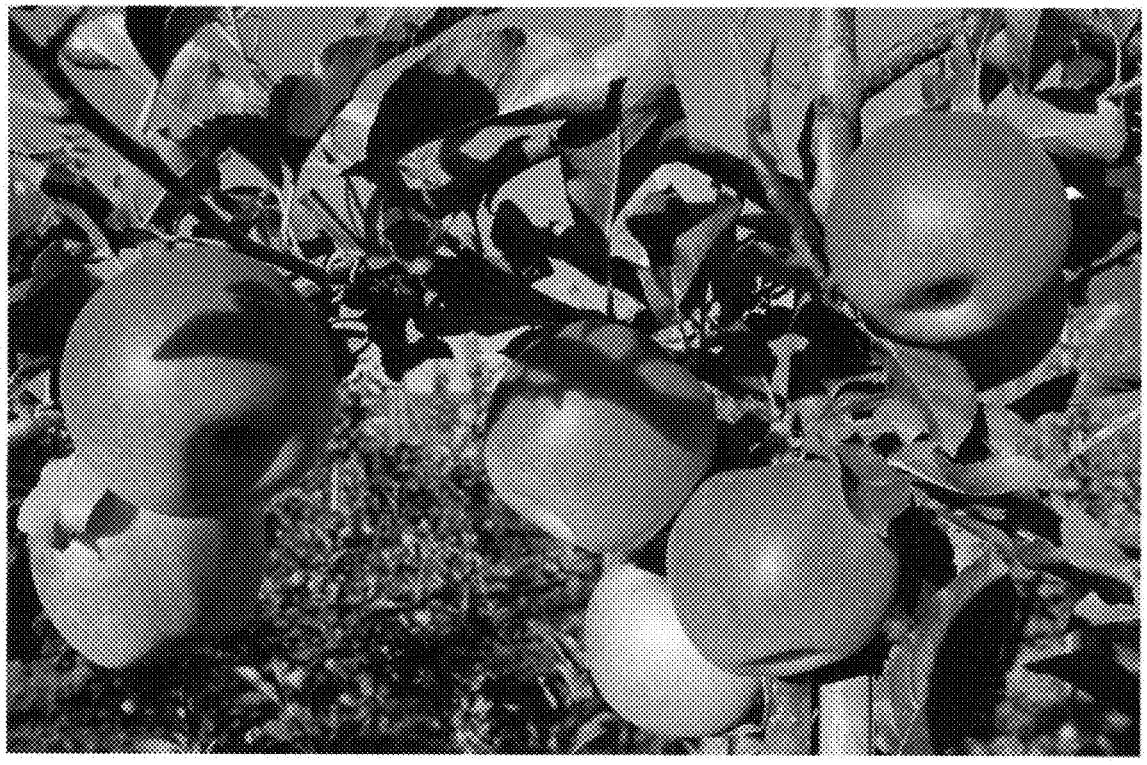
Figure 3:
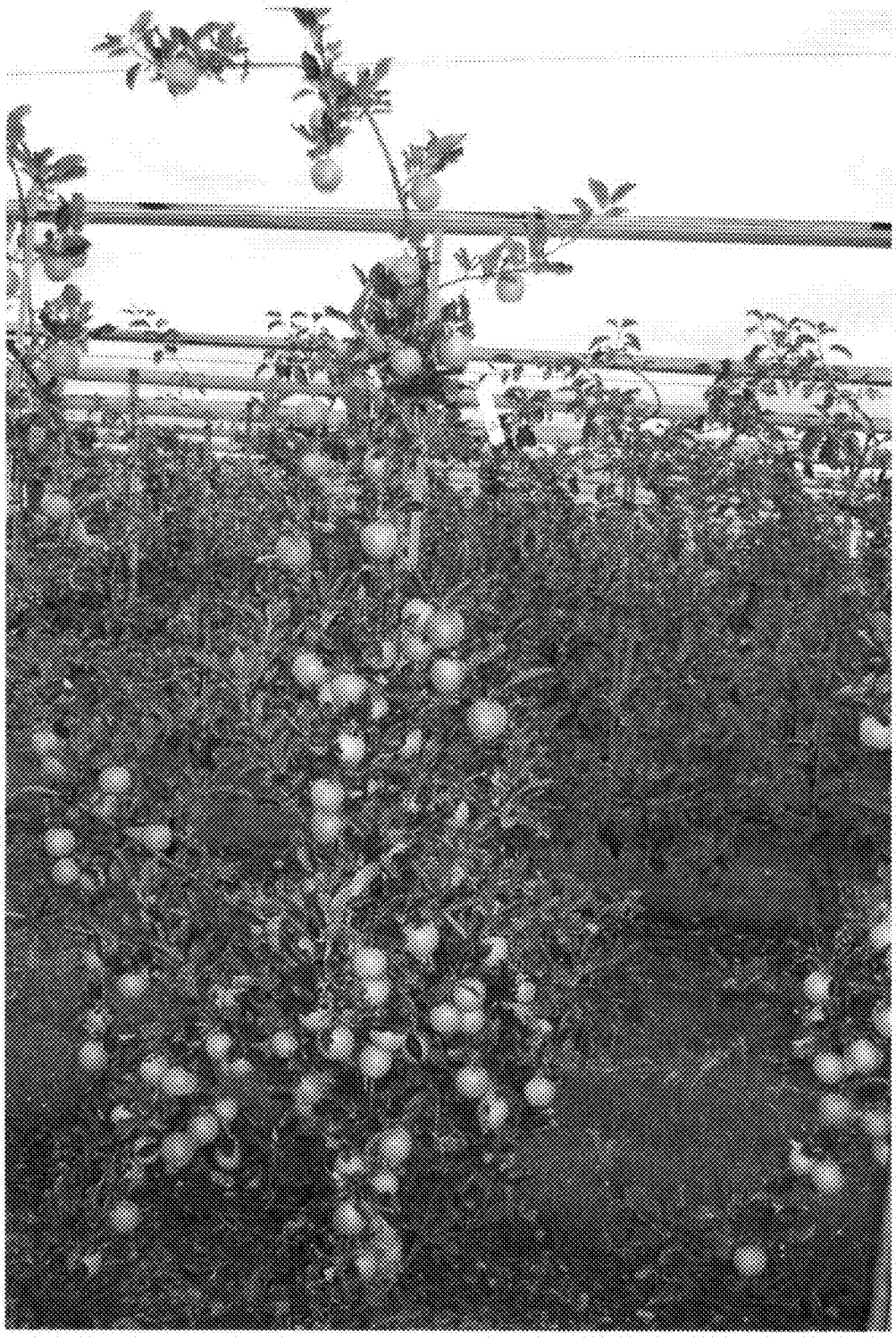
Figure 4:
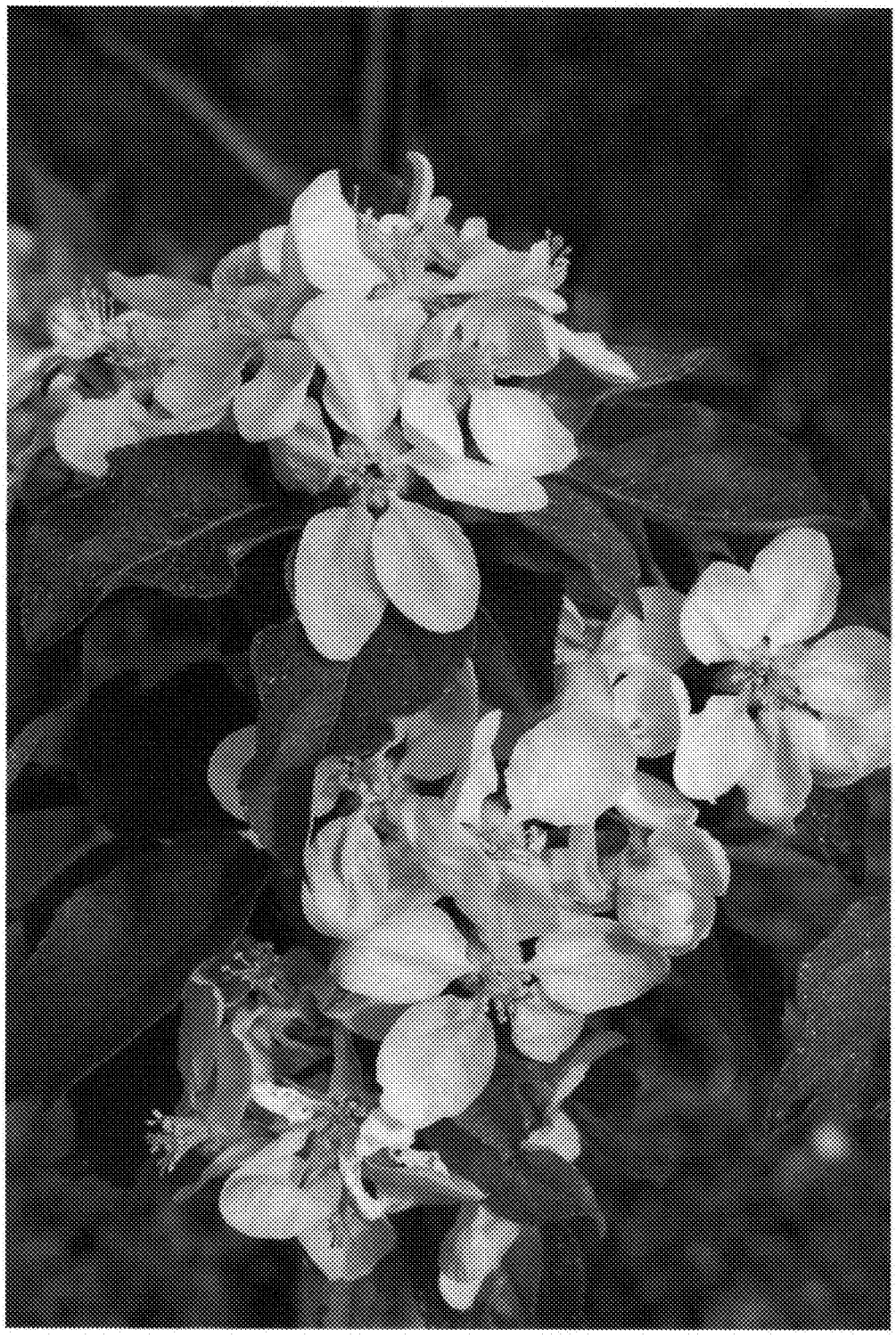
Figure 5:
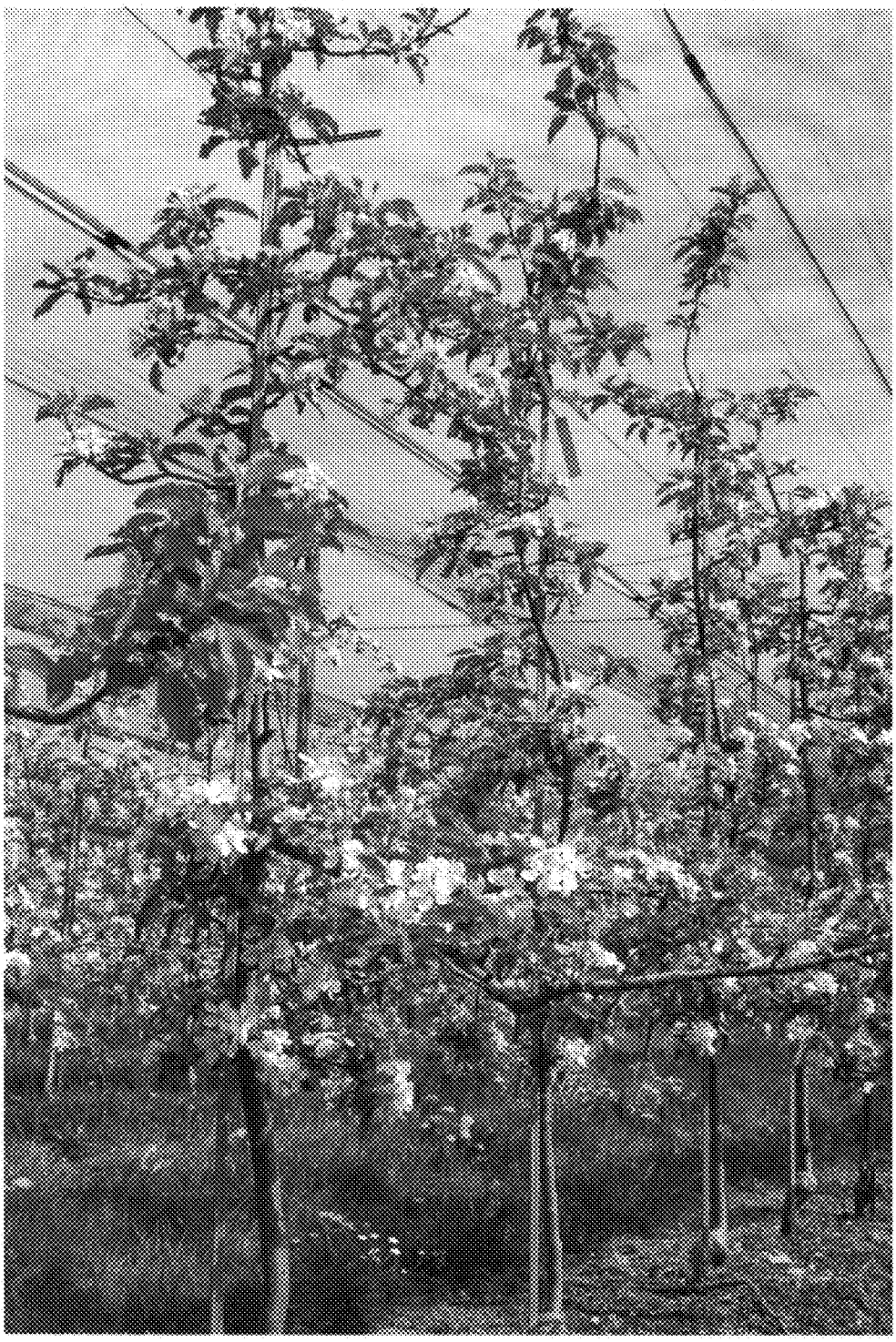
Figure 6:
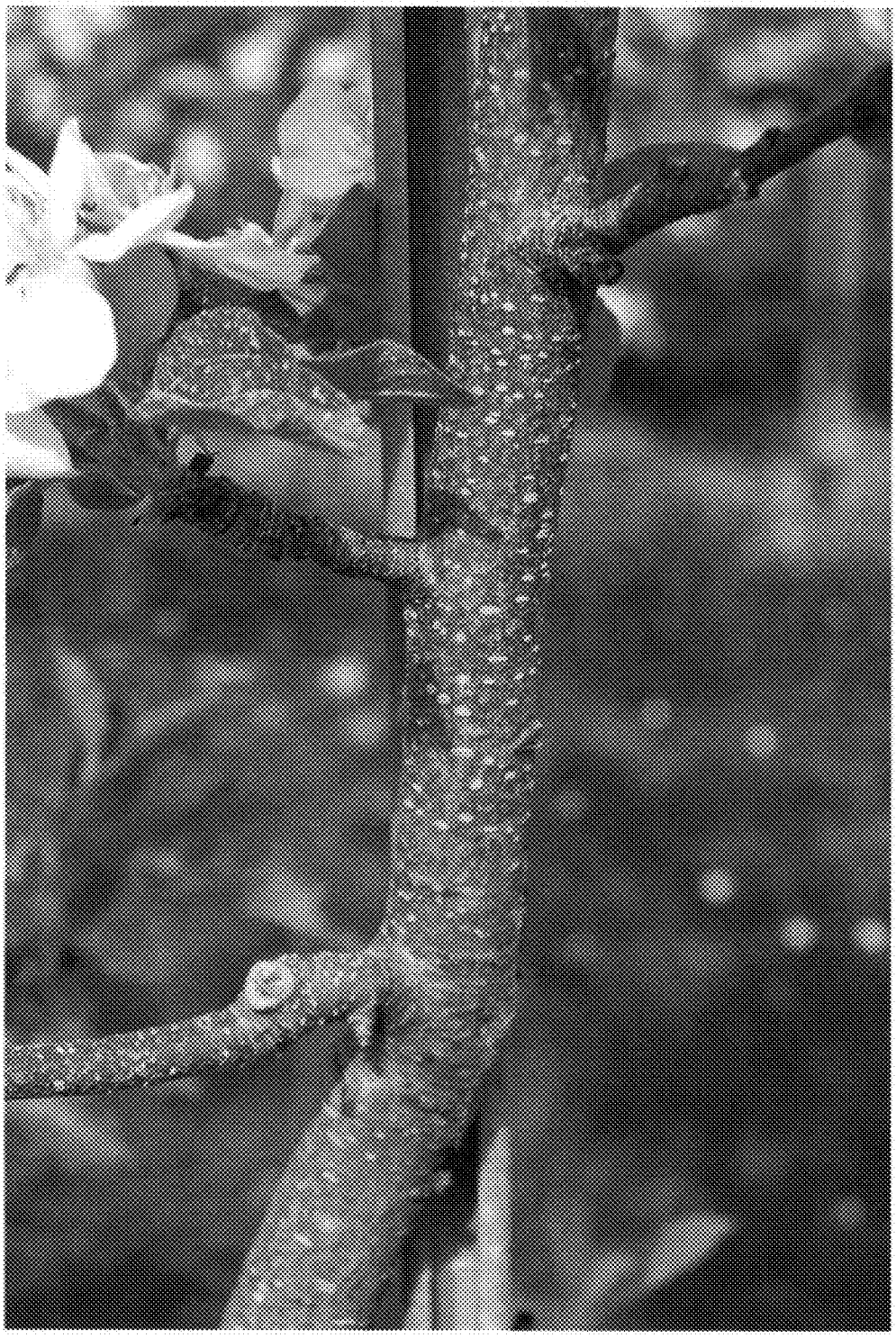

FIG. 1 is a photograph of the fruit of the variety;
FIG. 2 is a photograph of the fruit, leaves and trunk of the variety;
FIG. 3 is a photograph of a tree of the variety;
FIG. 4 is a photograph of the blossoms and leaves of the variety;
FIG. 5 is a photograph of a tree of the variety in bloom; and
FIG. 6 is a close-up photograph of the trunk and branches of the variety.

DETAILED BOTANICAL DESCRIPTION OF THE VARIETY

The following-detailed botanical description is based on observations made during the 2008 through 2011 growing seasons at Wädenswil, Switzerland of 'CH 101' trees planted in 2004 on 'J-TE-E' rootstock (not patented). All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Weak to medium.
- *Type*.—Bearing on spurs and long shoots.
- *Habit*.—Spreading.
- *Height*.—3.5 m.
- *Trunk diameter* (*at* 30 *cm above the graft*).—3.2 cm.
- *Bark texture*.—Fine.
- *Bark coloration*.—Brown 199A.

Branch (fruiting branches located at around 1 m above the graft union):
- *Length*.—1 m.
- *Diameter*.—1.6 cm.
- *Crotch angle*.—90°.
- *Bark color*.—Light brown N199C.
- *Lenticel length*.—1.5 mm.
- *Lenticel color*.—White 155D.
- *Number of lenticels per cm*$^2$.—8.

One year old shoot:
- *Length*.—40 cm.
- *Color*.—Red brown 172A.
- *Pubescence*.—Weak.
- *Thickness*.—0.6 cm.
- *Internode length*.—2.3 cm.
- *Pubescence*.—Weak.
- *Number of lenticels per cm*$^2$.—8.

Flower buds:
- *Quantity per spur*.—2 to 3.
- *Shape*.—Conical.
- *Length*.—Medium 11 mm.
- *Diameter*.—Medium 8 mm.
- *Color*.—Pink 63B.

Flowers:
*Diameter of fully open flower*.—41 mm.
*Relative position of petal margin*.—Free.
*Number per cluster*.—5 to 6.
*Date of first bloom*.—April 2.
*Date of full bloom*.—April 9.
*Pollination requirement*.—Pollinator required; such as 'Golden' or 'Braeburn'.

Petals:
*Quantity per flower*.—5.
*Shape*.—Ovate.
*Length*.—Long, 17 mm.
*Width*.—Wide, 12 mm.
*Apex*.—Round.
*Base*.—Pointed.
*Margin*.—Smooth.
*Coloration of upper surface*.—White N999D with pink vein 70C.
*Coloration of lower surface*.—White N999D with pink vein 70C.

Pistils:
*Size*.—13 mm.
*Color*.—Yellow green 145B.

Stigma:
*Size*.—1 mm.
*Color*.—Light yellow 8C.

Style:
*Size*.—10 mm.
*Color*.—Yellow green 145B.

Ovary:
*Size*.—5.5 mm.
*Color*.—Light green 141D.

Anthers:
*Quantity*.—Numerous, 12 avg.
*Size*.—2 mm.
*Presence of pollen*.—Yes.
*Color of pollen*.—Light yellow 8C.

Pedicel:
*Length*.—22 mm.
*Diameter*.—Thin, 1.6 mm.
*Color*.—Light green 141D.

Sepals:
*Quantity*.—5.
*Coloration*.—Light green 141D.
*Shape*.—Conical pointed.
*Margin*.—Smooth.

Leaves:
*Shape*.—Ovate.
*Length*.—Medium 98 mm.
*Width*.—Medium 54 mm.
*Length/width ratio*.—Medium.
*Blade margin*.—Serrate.
*Apex*.—Acuminate.
*Base shape*.—Irregular.
*Color of upper surface*.—Dark green 136A.
*Color of lower surface*.—Whitish green 137C.
*Attitude in relation to shoot*.—Outward.

Petiole:
*Length*.—3.2 cm, long.
*Diameter*.—2 mm, thin.
*Coloration*.—Green.

Fruit:
*Quantity per cluster*.—1 to 3.
*Diameter*.—78 mm.
*Weight*.—185 g.
*Ratio of height to width*.—Medium.
*General shape in profile*.—Globose.
*Position of maximum diameter*.—Toward petiole.
*Ribbing*.—Moderate.
*Crowning at calyx end*.—Moderate.
*Size of eye*.—Large.
*Aperture of eye*.—Closed.
*Length of sepal*.—Long.
*Bloom of skin*.—Absent or weak.
*Greasiness of skin*.—Absent or weak.
*Background color of skin*.—Light yellow 8C.
*Amount of over color*.—Medium.
*Over color of skin*.—Orange-red 41B.
*Intensity of over color*.—Medium.
*Pattern of over color*.—Flushed, striped and mottled.
*Amount of russet around stalk cavity*.—Absent or small.
*Amount of russet on cheeks*.—Absent or small.
*Area of russet around eye basin*.—Absent or weak.
*Length of stalk*.—Medium to long.
*Thickness of stalk*.—Thick.
*Depth of stalk cavity*.—Medium.
*Width of stalk cavity*.—Medium.
*Depth of eye basin*.—Medium.
*Width of eye basin*.—Medium.
*Firmness of flesh*.—Firm.
*Flesh texture*.—Fine.
*Aroma*.—Sweet.
*Juiciness*.—Very juicy.
*Brix*.—15°.
*Flesh coloration*.—Light yellow 4D.
*Stem coloration*.—Green-brown 152B.

Seeds:
*Quantity per fruit*.—3 to 16.
*Shape*.—Elongated oval.
*Coloration*.—Dark brown 200B.

Harvest:
*Time for harvest*.—End of September (first pick 7-10 days before Golden Delicious).
*Number of picks*.—3.
*Amount of fruit produced per tree per harvest*.—30.

Disease resistance/susceptibility: Scab resistant (Vf-resistance), susceptible to *Nectria canker*, powdery mildew (*P. lecotricha*).

Market use: Table fruit.

I claim:

1. A new and distinct apple tree substantially as described and illustrated herein.

* * * * *